United States Patent [19]

Mick

[11] Patent Number: 5,241,965
[45] Date of Patent: Sep. 7, 1993

[54] CARDIAC MONITOR

[76] Inventor: Peter R. Mick, 4 Stonybrook Trail, Kinnelon, N.J. 07405

[21] Appl. No.: 712,049

[22] Filed: Jun. 7, 1991

[51] Int. Cl.$^5$ .............................................. A61B 5/029
[52] U.S. Cl. .................................... 128/713; 128/637; 128/691; 128/739
[58] Field of Search ............... 128/713, 637, 691, 694, 128/736

[56] References Cited

U.S. PATENT DOCUMENTS

3,847,142 11/1974 Williams, Jr. et al. .............. 128/694
4,437,469 3/1984 Djordjevich et al. ............... 128/713

*Primary Examiner*—William E. Kamm
*Assistant Examiner*—Scott M. Getzow
*Attorney, Agent, or Firm*—Alfred C. Hill

[57] ABSTRACT

A non-invasive cardiac output and left ventricular ejection volume monitor system comprising a first arrangement disposed on a given portion of a patient's body having a fluid passageway therein in juxtaposition with the given portion of the body; a second arrangement coupled to an inlet of the passageway to cause a fluid to continously flow therethrough at a controllable input temperature and flow rate; and a third arrangement coupled to the second arrangement and an outlet of the passageway to determine energy transferred between the fluid and the given portion of the body, the determined energy transfer being a measure of cardiac output. A fourth arrangement disposed at an extremity of the body and coupled to the third arrangement, the fourth arrangement measuring the heart rate of the body and the third arrangement dividing the cardiac output by the heart rate to provide an indication of the left ventricular ejection volume.

20 Claims, 5 Drawing Sheets

CARDIAC MONITOR

BACKGROUND OF THE INVENTION

The present invention relates to cardiac monitors and more particularly to a non-invasive cardiac output and left ventricular ejection volume monitor system.

The need for the measurement of cardiac output is well established. Volumetric blood flow is clearly an important if not the most important measurement in circulation. The need for this measurement is well documented in the medical literature by the voluminous amount of work directed at discovering a tractible method of achieving the result.

Although dozens of methods have been worked on with varying degrees of success, and involving a copius variety of technologies, the ultimate test of their efficacy is in their utilization.

Currently the methods most employed are;

1. Ultra Sound—An esophageal doppler ultrasonic transducer is used to measure the flow rate in the lumen of the ascending aortic arch plus image the lumen at the site of the flow rate measurement. The product of average flow rate times the lumen area yielding cardiac output.

Problems associated with this method are: (a) motion in the lumen due to the pulsitile blood flow, (b) turbulent artifacts in the doppler measurements complicating the determination of the average flow across a systalic interval, (c) cost of equipment, and (d) invasive nature of the method.

2. Thermal Dilution—Placement of a catheter, entering thru the internal jugular vein, generally flow directed, thru the right heart terminating several centimeters into the pulminary artery. A bolis of cool water is then injected into the atrium where it mixes with the venus blood in the right heart and pulminary artery. A heat sensing device (thermister, thermocouple) then measures and integrates the resulting thermal profile as a function of time until the core temperature is detected. From the thermoprofile, volume and temperature of the water bolis, and the specific heat of water and blood, cardiac output is computed.

Problems associated with this method are: (a) errors resulting from incomplete mixing (high or low errors), (b) response time of the transducer causing errors, (c) resolution of the transducer, (d) placement of the transducer (i.e. contacting inner wall of pulminary artery), (e) heat losses thru conduction in myocardia and internal structures of the heart as well as the pulminary arterial wall, (f) measurement accuracies i.e. volume and temperature of the bolis at the site of injection, (g) variations in the transit time of the mixture due to synchronization with the systole, and atrial and ventricular retention at end diastole, and (h) risks associated with such a highly invasive procedure.

3. Indicator Dilution—An indicator capable of being tolerated by the patient and at the same time capable of modifying the electrical, optical, thermal, or radioactive characteristics of the blood, is injected into a vessel or compartment. Subsequently samples are drawn or by continuous non invasive monitoring (optical densitometers, scintillation counters) measurements are made of the concentration as a function of time.

Integrating the samples as a function of time, each sample, or time interval, presenting a "density" $\delta(t)$ at a specific time i.e. the volume of indicator present in the sample divided by the sample volume, provides the ratio of the volume of injected indicator (I) to the flow (F).

$$\int_{t_i}^{t_f} \delta(t)dt = \frac{I}{F}$$

The integration is performed in a manner that accounts for all injected material. Problems associated with this method are: (a) recirculation destroying the "tail" of the wash out curve, (b) sensitivity of concentration sensing transducers, (c) patient tolerance to the injected material, (d) accuracy considerations related to accounting for all of the injected material i.e. compartments with multiple discharges, when the flow path involves several organs, recirculation may occur in shorter path prior to the initial injection indicator returning thru the longer desired paths to the measurement site, elimination of indicator thru absorption, excretion, and (e) invasive nature of procedure.

U.S. Pat. No. 4,569,355 discloses a non-invasive method to monitor peripheral blood flow employing a heat exchanger that changes the temperature of a predetermined area of the skin at a programmed rate preferably by cooling. The rate at which the area of skin changes in response to temperature change of the heat exchanger and the rate the skin temperature returns to normal are then measured and compared to standard rates over a number of cycles. In this method, the temperature of the skin and the change of temperature of the skin are measured to determine if the peripheral blood flow is impaired.

SUMMARY OF THE INVENTION

An object of the present invention is to provide an improved cardiac output and left ventricular ejection volume monitor system that obviates the above-mentioned problems of the above-mentioned presently employed invasive methods and improves upon the technique of the above-cited patent by employing a technique that is non-invasive, repeatable, monitors on a continuous basis, providing cardiac output and left ventricular stroke or ejection volume with prescribed accuries.

A feature of the present invention is the provision of a non-invasive cardiac output and left ventricular ejection volume monitor system comprising first means disposed on a given portion of a patient's body having a fluid passageway therein in juxtaposition with the given portion of the body; second means coupled to an inlet of the passageway to cause a fluid to continuously flow therethrough at a controllable input temperature and flow rate; and third means coupled to the second means and an outlet of the passageway to determine energy transferred between the fluid and the given portion of the body, the determined energy transfer being a measure of the cardiac output.

Another feature of the present invention is the provision of a fourth means disposed at an extremity of the body and coupled to the third means to measure the heart rate of the body, the third means dividing the cardiac output by the heart rate to provide an indication of the left ventricular ejection volume.

Still another feature of the present invention is the provision for control of the flow of blood through the first means and/or for the control of the rate of flow and temperature of the fluid flowing through the passageway to impart a selected one of impulse, step and ramp functions thereto to enhance measurement of the cardiac output.

The following is provided to lend insight as to the nature of the energy exchange being described.

If a normal human hand was submerged in an insulated container with a liquid of known thermal characteristics, and the liquid was at a different temperature than the hand, after a period of time the liquid would become the same temperature as the hand. The source of heat energy being the circulating blood in the hand. The energy exchanged is capable of being accurately calculated knowing the volume, initial temperature and thermal characteristics of the liquid.

If the same experiment is performed with a non-insulated container, the temperature of the liquid will equilibrate with the environment and the hand at a temperature between the blood's core temperature and the ambient. Once the temperature of the liquid is constant, the heat losses from the container (which is calculable and measurable) are equal to the heat losses from the flowing blood.

If the blood volume flow rate changes, the equilibrated temperature of the liquid changes. If the flow rate stops and conduction losses thru the arm are accounted for, the temperature of the liquid approaches room ambient.

The present invention expands on these concepts to allow for precise absolute blood flow measurements and methods of taking continuous measurements without the need for precise calorimeters or long time delays waiting for thermal masses to arrive at equilibrium.

BRIEF DESCRIPTION OF THE DRAWING

Above-mentioned and other features and objects of the present invention will become more apparent by reference to the following description taken in conjunction with the accompanying drawing, in which:

FIGS. 3A–3F are a series of graphs useful in explaining the principles of the present invention;

DESCRIPTION OF THE PREFERRED EMBODIMENTS

A technique is disclosed that allows a heat exchanger (thermal sensor unit), referred to hereafter as TSU, to contact the surface of the skin (epidermis), and thru heat conduction cause thermal energy to be transferred to the blood (if the TSU is above normal body temperature), or from the blood (if the TSU is below the normal body temperature). The magnitude of this energy transfer is directly measurable from the TSU.

The TSU temperature is controlled by a fluid flowing through the TSU. For purposes of illustration, the remaining description will refer to a liquid but a gas could be used in place of the liquid. Both the incoming liquid temperature and flow rate are precisely controlled. The TSU has a controllably low thermal mass, with high thermal conductivity at the area of contact to the epidermis, and low thermal conductivity at all other outer surfaces.

The energy exchanged is a measure of blood flow rate. The measurement of the energy transferred to the liquid can be measured by: calculating BTU's (British Thermal Units) gained or lost by knowing; the temperature change that occurred, the volume of liquid that the temperature change occurred in, and the specific heat (c) of the liquid, or by heating or cooling the liquid leaving the heat exchanger in a manner that allows its temperature to be restored to the original inlet temperature of the TSU. The energy required to accomplish this is equal to the energy transferred from the blood flow.

The above measurement can be additionally enhanced by taking transient measurements which aid in characteristizing the thermal conductivity of the dermus, subcutaneous, and deep fascia at the TSU site, by measuring the time domain responses of the TSU to; impulses, step functions and ramps etc. These can be introduced into the flow rate of blood by using an inflatable cuff proximal to the TSU capable of pressure controlled inflations up to and including the local systolic pressure, providing flow rate control from unrestricted to totally occluded at the TSU.

Excitations, as a function of time, of a similar nature can be introduced into the TSU liquid in the form of both temperature and flow rate.

Knowing the nature of the exitation(s) and the TSU response as a function of time allows conventional time and frequency domain analysis techniques to be used to characterize the system conductivity.

The patients cardiac output (CO) is determined from:
(1) the continuous flow measurement,
(2) characterizing the conductivity as a result of transient measurements,
(3) accessing a data base that was generated from a large sample of data from patients who have been categorized by variables such as the following: (a) actual CO, (b) TSU flow rate at selected TSU site, (c) characterized conductivity at TSU site by transient measurements, (d) skin temperature, (e) room temperature, (f) age, (g) sex, (h) race, (i) height, (j) bone structure, (k) weight, (l) surface area, etc., and,
(4) processing the present patient data with data base information to determine most probable CO, including an accuracy estimate of the reading.

Still another advantage of the invention is the ability to provide real time left ventricular ejection volume (LVEV) measurements. This is achieved by first noting that average CO (i.e. liters/min) divided by heart rate yields average LVEV (LVEV). By use of an optical densitometer, either reflective or transmissive, measuring vascular perfusion at an extremity i.e. pinna, finger, etc. and during each systolic pulse integrating the optical density thru the entire period. The sum of the itegrations over a one minute interval divided by the heart rate (HR) yields a measure of the average integrated optical density value per systole. The individually integrated value for each systole is monotonically related to the amount of perfusion per stroke and therefore "flow" for each systole. On an individual systole basis the integrated optical density, thru the monotonic relationship is converted to a number that is proportional to perfusion volume. The percentage deviation this number has from the mean perfusion volume is the % deviation the LVEV deviates from the average LVEV ($\overline{LVEV}$). Therefore LVEV is known on a per stroke basis and can be displayed.

The human body, in a warm environment contains a high degree of thermo regulation and internally is approximately isothermal (98.6 F.). The main cause of the isothermal characteristic is the volumetric flow of blood, communicating (adding and removing) heat from various organs and elements. The energy source for the heat is foodstuffs which produce heat thru: (1) basal metabolism, (2) muscular activities (work), involuntary and voluntary, (3) hormones (Adrenaline, thyroxin) effect on cellular metabolism, and (4) temperature effects on metobolic rate. This is balanced by heat losses mainly thru: (1) radiation (surface area), (2) evaporation (skin, respiration), (3) respiration, (4) convection, and (5) conduction. All of these are sensitive to ambient conditions; temperature, humidity, air velocity, etc.

The objective of the present invention is to produce a local change in the normal heat balance by forcing thermal energy to be exchanged with a small region of body mass. This is accomplished by providing a contacting surface to the skin at the site of the measurement of specific are $A_s$ and approximately isothermal temperature $T_s$. The contacting surface can consist of a thin sheet of highly conductive material, such as copper and its temperature is controlled by a flow $F_L$ of liquid with known specific heat, density and thermal conductivity, $c_L$, $s_L$ and $k_L$, respectively. The flow is sufficiently high so that the surface remains very close to the inlet temperature of the liquid, relative to the core temperature of the tissue mass.

The effect of this surface is to set up a temperature gradient between the "core" temperature of the body element and the surface area. The shape of the temperature gradient being dependent on the geometry of the specific anatomical region as well as the thermal conductivity within the intervening tissue mass containing the cutaneous vasculature with cellular metabolic energy exchanges and vasodilatory responses as well as the deeper bone masses, arterial and venus blood flows etc. Considering a region such as the forearm, the net blood flow across a radial section is zero.

After equilibrium the temperature distribution radially is time independent as well as the temperature distributions within the arterial and venus blood flows (neglecting pulsetile variations in the thermal inertia of the contact surface and intervening tissue averages the effect). Obviously if the blood flow ceased the core temperature would start to change, the radial temperature distribution would shift and after equilibrium the energy exchange would be different causing the temperature difference between the inlet and outlet temperatures $\Delta T_s$ of the contact surface to change.

Figure 1:
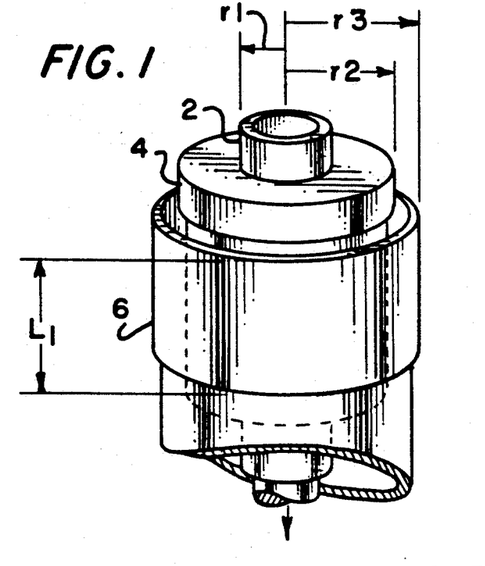
FIGS. 1 and 2 illustrate the relationship between an extremity of a human body and a heat exchanger useful in explaining the principles of the present invention.

FIG. 1 shows a simple model of the situation.

The core 2 carries a flow $F_B$ of blood (specific heat $c_b$, density $S_B$ and conductivity $K_B$) at a temperature $T_B$. A water jacket 6 carries a flow of water $F_w$ and a temperature gradient is established in the conductive medium 4 between the two flows. The flow rates are considered sufficiently high that the temperature drops across the two flows are small relative to the temperature difference $T_B - T_W$. The governing relationship is the differential heat flow equation;

$$\nabla \cdot \nabla T = (co/k)(dT/dt)$$

which in cylindrical coordinates becomes;

$$(\delta^2 T/\delta Z^2) + (1/r)(\delta/\delta r)(r\delta T/\delta r) + (1/r^2)(\delta^2 T/\delta \theta^2) = (co/k)(dT/dt)$$

which for the equilibrium case (i.e. the temperature is constant at any given location and the temperature variation is only radial) becomes $$(1/r)(\delta/\delta r)(r\delta T/\delta r) = \delta^2 T/\delta r^2 + \delta T/r\delta r = 0.$$

Therefore:

$$dT/dr = c_1/r$$

and $$T = c_1 \ln r + c_2$$

From the boundary conditions:

$$[d\ r = r_3\ T = T_w,\ [d\ r = r_1\ T = T_B$$

$$c_1 = (T_B - T_w)/\ln(r_1/r_2)$$

$$c_2 = T_B - \frac{(T_B - T_w)}{\ln(r_1/r_2)} \ln(r_1).$$

The gradient (heat transferred per unit area per unit time) is $$d\dot{Q} = K\frac{dT}{dr} = K\frac{(T_B - T_w)}{\ln(r_1/r_2)} \cdot \frac{1}{r}\ dA.$$

Heat transferred at $r=r_2$, over length $L_1$ where;

$$dA = r_2 d\theta dl$$

is $$\dot{Q} = \int_0^2 \int_0^{L_1} \frac{K(T_B - T_w)}{\ln(r_1/r_2)}\ d\theta dl$$

or $$\dot{Q} = 2\pi L_1 K(T_B - T_w)/\ln(r_1/r_2)$$

If in the example the water temperature is below that of the blood, the above expression describes the heat gained, per unit time by the water. In order for the water to remain at essentially a constant temperature relative to the temperature difference between the water and blood, a relatively rapid flow is required.

The heat required to raise a mass (m) of a substance at a given temperature ($\Delta T$) is;

$$\dot{Q} = cm\Delta T$$

or per unit time with a fixed $\Delta T$ $$\frac{d\dot{Q}}{dt} = c\Delta T \frac{dm}{dt} = c\delta\Delta T \frac{dv}{dt} \quad \text{Where } \delta = \Delta m/\Delta V$$

or $$\dot{Q} = c\delta \Delta TF.$$

Therefore:

$$\dot{Q} = \frac{2 L_1(T_B - T_w)}{\ln(r_1 r_2)} = c_w s_w \Delta T_w F_w$$

In the steady state the energy gained by the water was lost from the bloods thermal mass, (plus some heat exchange as a result of local endo and exothermic metabolic reactions, catabolism and anabolism). The rate of heat flow from the blood equals the heat flow into the water, therefore the heat flow (in steady state) thru the perfused tissue mass must equal the energy flows, from and to, the blood and water respectively.

Namely:

$$\dot{Q}_B = -c_B s_B \Delta T_B F_B = C_B \Delta T_B F_B \quad (A)$$

$$\dot{Q}_w = +c_w s_w \Delta T_w F_w = C_w \Delta T_w F_w \quad (B)$$

$$\dot{Q}_F = 2\pi k(\overline{T}_B - \overline{T}_w)/\ln(r_1/r_2) = K(\overline{T}_B - \overline{T}_w) \quad (C)$$

The blood flow, conductivity, specific heat and geometry remains the same for a series of measurements on the same patient. The measurements of $\dot{Q}_w$, calculated from the measurement of $\Delta T_w$ and $T_w$ allow $F_B$ to be calculated. $\Delta T_w$ is the average of the inlet and outlet water temperatures. $\Delta T_B$, has two components; the venus blood and the arterial blood temperature losses. The arterial blood temperature (core temperature $T_c$) entering the monitoring site can be considered a constant, i.e. $T_c = 98.6$ F., since due to the small energy loss associated with measurement, the visceral core temperature will not shift. The arterial blood leaving the distal portion of the site will experience a temperature loss $\Delta T_B$. The venus blood arriving at the site will be in the range of $T_c$ to $(T_c - \Delta T_B)$ depending on whether or not it has been rewarmed by metabolic regulatory actions, or has experienced no rewarming. It is assumed that additional cooling of the blood in the extremity has not occurred. Convection, radiation, and conduction losses can be minimized by covering the extremity with a thermally insulating material, if needed.

If the venus blood has been restored to the core temperature it will experience a $\Delta T$ similar to the arterial blood. If the blood is not rewarmed it will experience an additional temperature drop of $\Delta T$ leaving the proximal side of the measurement site with a temperature of $T_c - 2\Delta T_B$.

Since the volumetric flow rate of venus blood at the measurement site equals the flow rates of arterial blood at the measurement site (i.e. the mass of the extremity does not change) the average arterial temperature is $T_c - \Delta T_B/2$, and the "non-rewarmed" venus blood temperature is $T_c - 3\Delta T_B/2$, and the "warmed" venus blood temperature is $T_c - \Delta T/2$.

The average temperature for the rewarming case is;

$$T_B = \tfrac{1}{2}(\overline{T}_V + \overline{T}_A) = T_c - \Delta T/2$$

(equal volumes) and for the no rewarming case is $$T_B = T_c - \Delta T_B.$$

$T_B$ can be considered to be $\Delta T_B/a$, where a is a constant that is between 1 and 2, depending on the degree of rewarming.

The three previous relationships can be rewritten as;

$$\dot{Q}_B = {}^*C_B F_B(\Delta T_B)$$

$$\dot{Q}_w = C_w F_w \Delta T_w$$

$$\dot{Q}_H = K(T_c - T_w - {}^{}\Delta T_B/a + {}^{}\Delta T_w/2)$$

*$F_B$ is twice the arterial flow
**average temperature losses

After equilibrium $\dot{Q}_w$ represents the amount of heat flow required to stabilize the system (i.e. heat distributions are independent of time). The heat liberated from the blood equals the heat absorbed by the water. The magnitude of the flow being related to the difference in temperature, the physical geometry of the heat paths and the path conductivity. The heat flowing into the water is:

$$\dot{Q}_w = c_w F_w \Delta T_w = K(T_c - T_w - \Delta T_B/a + \Delta T_w/2),$$

$\Delta T_w$ being the difference between the inlet and outlet temperatures of the heat exchanger or water jacket 6.

A change in flow rate in heat exchanger 6 causes an inverse change in $\Delta T_w$, but the heat exchanged remains constant. If both the blood flows and water flows could be made arbitrarily high (not practical for a living organism, but experimentally feasible thru simulations)

$$\dot{Q}_w = c_w F_w \Delta T_w = \operatorname{Lim} K(T_c - T_w - \Delta T_B/a + \Delta T_w/2)$$
$$F_w \to \infty$$
$$F_B \to \infty$$
$$\Delta T_B \to 0$$
$$\Delta T_w \to 0$$
$$\dot{Q}_w = K(T_c - T_w)$$

The heat exchanged is independent of the flow rate, only the $\Delta TF_w$ product changes. K is independent of both the flow rate and $\Delta TF_w$ and can therefore be calculated from the above relationship.

"a" must be experimentally determined but will be repeatable from subject to subject, unlike K that depends on the tissue, vascular bed geometry, the nature of regional perfusion characteristics and regional chemistry.

After equilibration $\Delta T_w$, $T_w$, $F_w$ and therefore $\dot{Q}_w$ are known. The core temperature $T_c$ will be assumed to be normal deep arterial temperature, or can be measured. A reference value of K is then calculated as;

$$K_R = \dot{Q}_w/(T_c - T_w).$$

$K_R$ can serve as a "classifying" measurement in the data base, it also allows the blood flow $F_B$ to be calculated as $$F_B = 2\dot{Q}_w/aK_b\Delta T_w,$$

where the arterial flow is ($\tfrac{1}{2}$) $F_B$.

The above was based on a model as shown in FIG. 1 that has circular symmetry. Similar relationships can be found for other geometries such as shown in FIG. 2 indicating a region that is rectangularly symmetric, where K would be;

$$K = w l k / h.$$

Figures 2, 11:
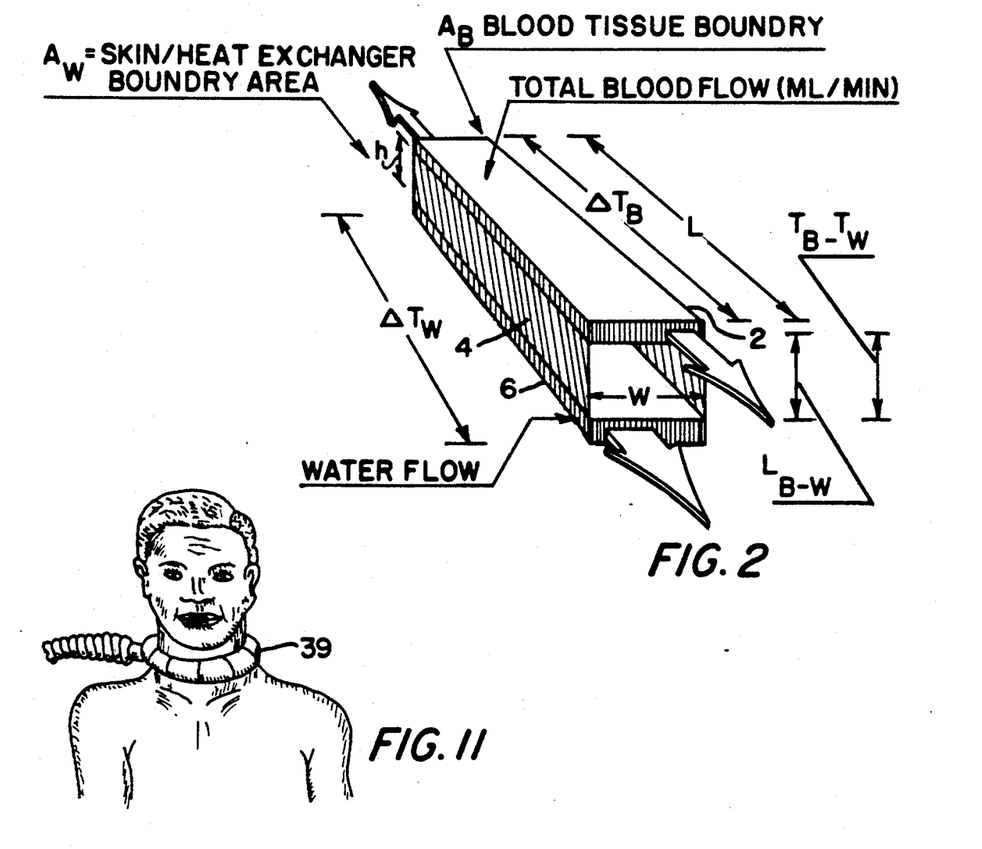
FIGS. 8, 9, 10, 11, and 12 illustrate variations of the cuff in FIG. 7 that may be employed in the overall system of FIG. 7.

The same reference characters are employed in FIG. 2 to identify the same components as in FIG. 1.

Since the heat flow can be thought of as streamlines of heat being directed between the veins and arteries (venules, arterioles and capalaries) and heat exchanger 6, these independent regions can be modeled independently representing arbitrarily small volumes in contact with the vasculature and with heat exchanger 6. Lateral heat exchange does not occur between the regions since the boundaries are at the same thermal potential and have identical gradients, therefore, even differences in conductivities between regions will not cause lateral heat exchange. Each region will have its own conductivity (K) and geometry $\times$ (G).

$$\Delta \dot{Q}_F = G K (T_B - T_w) \Delta A$$

Each one of these elements making a "small" contribution to the changes in temperature of the blood and the water. Total heat exchange being the sum of all of the elements, $$\begin{aligned} \dot{Q}_F &= \sum_{i=1}^{n(A)} G_i K_i (\overline{T_B} - \overline{T_w}) \Delta A_i \\ &= (\overline{T_B} - \overline{T_w}) G_i K_i \Delta A_i \\ &= K(\overline{T_B} - \overline{T_w}) = K(T_c - T_w) \end{aligned}$$

which is the previously described measurement.

In addition to the steady state measurement (equilibrated) several opportunities for making transient measurements exist. For example an impulse, step or ramp function can be introduced to the heat exchanger flow rate causing a response in $\Delta T_w$ and $\dot{Q}_B$. Similarly, a transient can be introduced into the heat exchanger inlet temperature $T_w$ which in turn causes a different response in the heat diffusion equation and $\dot{Q}_w$. Additionally, by use of a conventional pressure cuff as used on commercial sphignomanometers partial or total occlusions can be effected under program control to generate transient as well as steady state responses in the blood flow. These operations can be employed to further evaluate K, and to use the results as a classification factors in the data base. Conventional analysis techniques exist which allow for the quantitative determination of the transient system characteristics, allowing an impulse response to be estimated, which further characterizes the measurement.

An additional characteristic of the invention is to determine the real time ejection volume of the left ventricle (LVEV), in that is is frequently symptomatic of pathologies associated with the cardiovascular system.

The mean cardiac output $\overline{CO}$ is related to average LVEV ($\overline{LVEV}$) thru the average heart rate (HR). i.e.

$$\overline{LVEV} = \overline{CO}/\overline{HR}.$$

Variations exist in the cardiac output with each heart beat, as well as beat to beat variations in heart beat duration. During a systole the periferal vasculature is perfused with blood in an amount that is related to the local periferal resistance, vascular plexus volume and blood pressure. By placing an optical densitometer 34 in FIG. 7 on a periferal region i.e. finger, lip, pinna etc., a measure of increase of blood volume during systole is obtained. Curve A of FIG. 3 indicates the diastolic pressure waveform, and curve B of FIG. 3 indicates the resultant peripheral flow at the densitometer monitoring site. The flow when integrated over the period of a heart beat provides a measure of the increase in blood volume at the monitoring site as shown in curve C of FIG. 3. Curve E of FIG. 3 illustrates the integrated optical density (IOD) waveform showing increase in blood volume as a result of the systole, as shown in the crosshatched portion of curve D of FIG. 3. The volume not crosshatched represents the optical density of the non pulsetile blood in the venus and capillary bed.

Figure 3A:
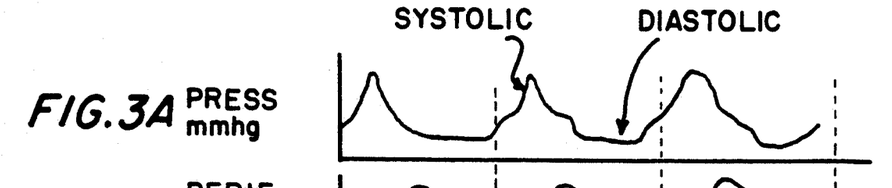
Figures 3C, 3D:
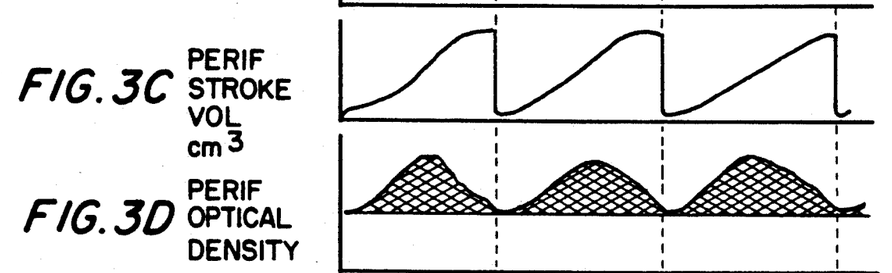
Figure 3E:
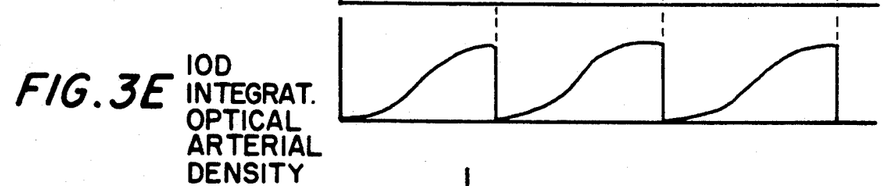
Figure 3F:
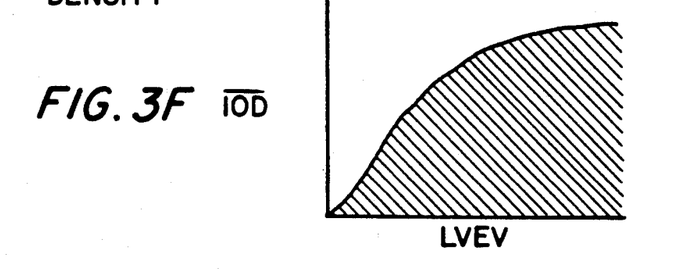

The IOD is monotonically related to the LVEV in that the higher the volume pumped, the greater the IOD at the monitoring site. Although the IOD cannot predict CO it can on the average be related to it thru the nonlinear but monotonic curve shown in curve F of FIG. 3. i.e.

$$\frac{(1/N) \sum_{i=1}^{N} (IOD)_2}{(\overline{CO}/\overline{HR})} = K(CO).$$
$N = \#$ of beats/min Different values of CO yield different values of K allowing curve F of FIG. 3 to be generated. When a single value of IOD is measured it can be converted directly into instantaneous LVEV. (i.e. as ml/stroke or % deviation from $\overline{LVEV}$.)

Another object of the invention is to provide a measurement of the peripheral resistance of the distal extremity from the heat exchanger 6 (i.e. finger, head, forearm, hand, foot etc.). This value is calculated by the ratio of average (mean) blood pressure:

$$\overline{BP} = \frac{1}{t} \int_0^t BP(t)dt,$$

which can be measured with a wide bandwidth pressure gauge. For example, by cuff pressure waveforms scaled to known systolic and diastolic values as shown in curve A of FIG. 3, measured conventionally. This value when divided by the CO (cm$^3$/sec) as previously determined provides peripheral resistance $$R = \frac{\overline{BP} \text{(mmhg) } 1332}{CO \text{ cm}^3/\text{sec}} = R \frac{\text{dynes/cm}^2}{\text{cm}^3/\text{sec}}$$

Figure 4A:
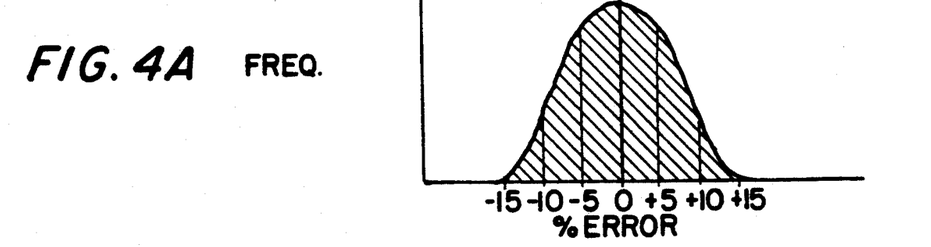
FIG. 4 is another series of graphs useful in explaining additional principles of the present invention.
Figure 4B:
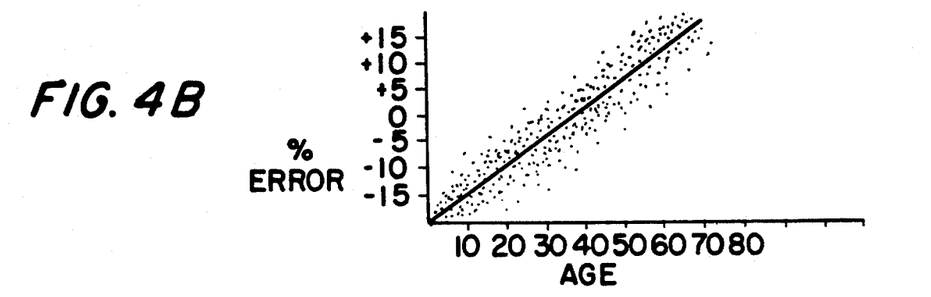
Figure 4C:
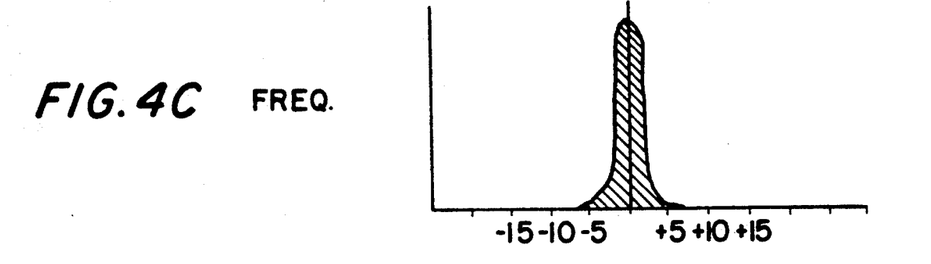

Another aspect of the present invention is its ability to refine its measurement accuracy by assessing a data base that contains data gathered from measured patients, of a multivariate nature, forming data points in a multidimensional space. For example, aging changes the bone mass of individuals relative to their body mass, and bony structures are in the heat flow path and certain nonlinear effects may be present. If a series of patients were tested and the results presented in terms of absolute percentage error as shown in curve A of FIG. 4 the instrument accuracy could be defined by its standard deviation. If the patients ages were plotted, in a scatter diagram, against % error as shown in curve B of FIG. 4 the correlation would be apparent. The systematic error can be computed as a correction factor for each age, and the measured value corrected. When the data are replotted, the error is substantially reduced as shown in curve C of FIG. 4.

Additionally these effects, as in the above example, can be related to gender, and could also be related to such other variables as; race, weight, bone structure (large, medium, small), surface area, hereditary predispositions, illnesses, height, etc.

In the data gathering process the patients actual CO, HR, and LVEV, using present invasive methods could be entered along with the measured values by the inventive monitoring system. Multiple cross correlations will be identified and the multivariate correction factors applied to each data point. Once all the correction factors have been applied and the systematic errors have been removed from the data base information, when a new patient is measured, those readings are adjusted by the same correction factors (relationships) that were applied to the data. It is recognized that as the number of variables increases the required data point sample size to achieve the same levels of significance in the overall accuracy (as determined with a lower number of variables) increases very dramatically.

Figure 5:
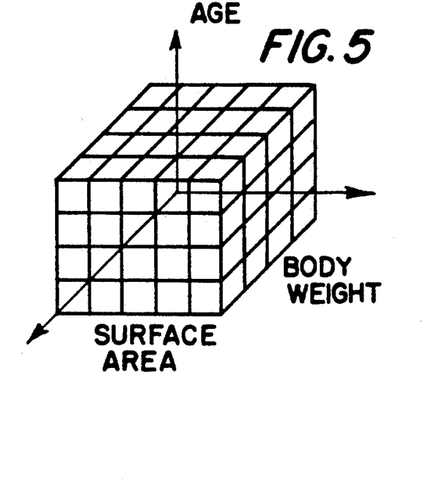
FIG. 5 is still another graph useful in explaining further principles of the present invention.

It is another object of this invention to place a measure of accuracy on the individual readings taken. The multivariate data base will define regions of high accuracy and low accuracy based on the "actual" versus "measured" data used in the data base. FIG. 5 depicts a region of three variates, age, surface area, and body weight. If each variable is subdivided into N ranges there would be $N^3$ rectangles, each rectangle containing the measured error information from the samples in that region. The error can be specified in terms of a standard deviation $\sigma$ relating to the differences between the measured and known data, all means will be zero as a result of uncorrelating the data. When a particular patient is being measured his attribute data will place him into a region and the tolerance associated with him will be specified with the instrument readings for that region.

For example, if during the establishment of the data base, one of the $N^3$ rectangles represented the following ranges; age 50-60 years, weight 160-180 lbs, surface area 1.8 to 2.2 sq. meters and 50 samples fell into that category. Each of these 50 samples (patients) would have had their CO measured by conventional means with known accuracy. Additionally, they would have had their CO measured at the same time with the device that is the subject of this invention. The difference between the two readings forming a data point.

Once the 50 data points have been determined, a mean value (bias error) is calculated and stored. A conventional standard deviation is calculated from the 50 data points and stored. This data is generated and stored for each of the $N^3$ rectangles, and forms the data base for the system of the present invention.

When the system is in the normal measurement mode, and is going to make a measurement, patient data is entered (i.e. weight, age, surface area) and a measurement is made. The measured value is then adjusted by removing the bias error stored in the cell defined by the patient data. This adjusted value is then displayed as the final value, and along with it is displayed the standard deviation calculated for that cell from the data base data. The standard deviation providing a conventional measure of accuracy, relative to the cardiac output standard.

The above considers only three input values, and in practice the number of variables will consist of those that contribute to the absolute accuracy as well as minimizing the error.

The purpose of the present invention is to find general application throughout the medical field. In order to meet diverse applications, many different requirements will be placed on its performance and configuration. In critical care, the requirements might be very high accuracy and reliability with minimal emphasis on cost and size. In hospital based patient monitoring systems, the focus would be on low cost, moderate accuracy, and compatibility with existing systems. In general practice, the focus would be on low cost, small size, reliability, ease of use. In medical mobile emergency care, the emphasis would be on ruggedness, reliability, operation readiness, low cost, ease of use and small size. Designs to achieve all of the above attributes can be effected by one skilled in the art, using the information here in provided.

From a system design viewpoint, there are two conceptual approaches to achieving the performance. One is the direct measurement of $\Delta T_w$, $F_w$ at the heat exchanger 6 (FIG. 1) and the direct calculation of $F_B$. This approach can provide wide bandwidth information in that the transient responses can be measured as a function of time, within the limitations of the thermal time constants of the temperature transducers and the heat exchanger itself.

Alternatively a heat exchanger or calorimeter approach may be employed to measure the amount of energy (BTU's) required to remove the heat from the circulating water (if water is used, and the inlet temperature of the heat exchanger 6 (FIG. 1) is below that of the body core temperature) by providing a thermal loss resistant flow path where the only significant thermal exchanges are the exchange between the body and the TSU, and the cooling heat exchange where the liquid is restored to its inlet temperature of the TSU.

This type of calormetric measure can be achieved thru several normal refrigeration methods. One that is particularly applicable is the use of peltier diodes whereby, due to the peltier effect, electrical power ($I^2R$) entering a PN diode causes one surface to heat and the other to cool. The heat pump mechanism is such that if the "hot" side of the junction is maintained at a constant and relatively accurate temperature, the cold side has the ability to pump heat at a precise rate, functionally related to the input power of the diodes and the cold side temperature. Therefore, using a watthour meter the energy exchanged with the incoming liquid can be precisely determined. The steady state flows are time independent i.e. at any location in the flow paths (internal/external), temperature is not changing with time.

Figure 6:
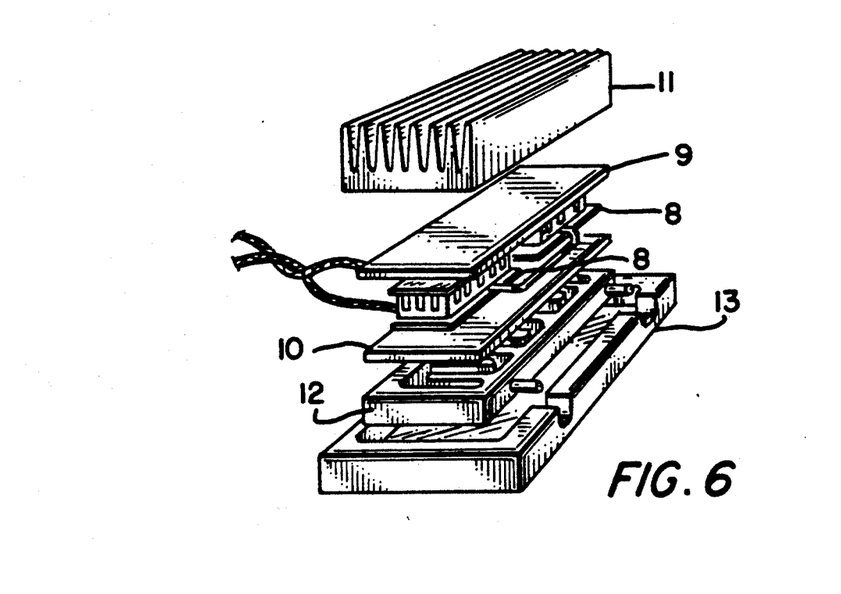
FIG. 6 is an exploded perspective view of a heat exchanger employed in an embodiment of the present invention.

FIG. 6 depicts the peltier diode heat exchanger. The diodes 8 are mounted between two heat conducting plates, a hot side plate 9, and a cold side plate 10. The hot side plate 9 is in intimate thermal contact with a heat sink 11 (or another exchanger) that maintains the hot side temperature at a constant value. The cold side plate 10 is mounted to the high conductivity liquid heat exchange flow chamber 12 which is surrounded by a thermal insulator 13.

Alternatively the design can be based on direct temperature measurements.

Figure 7:
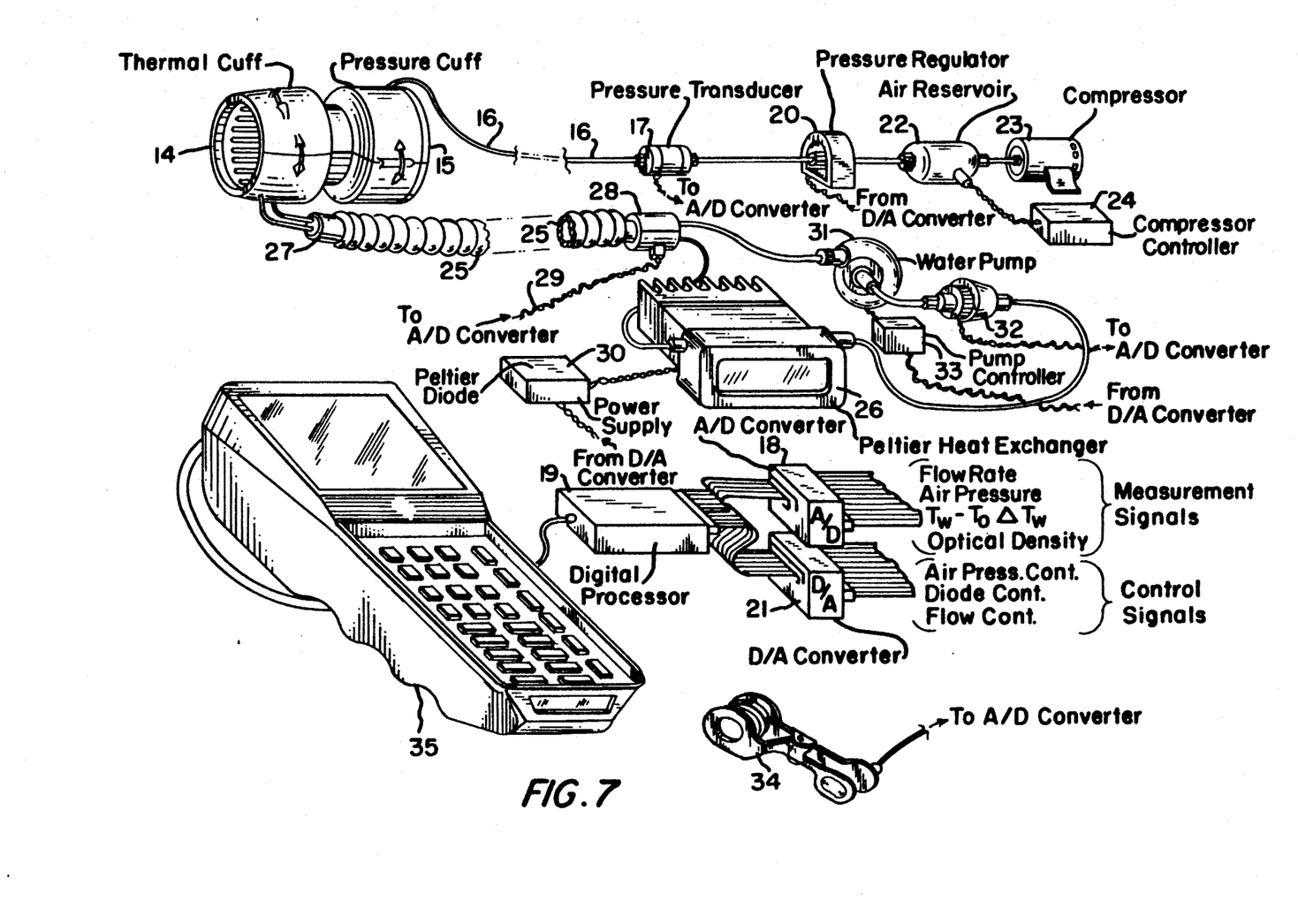
FIG. 7 if diagrammatic block diagram of an embodiment of the non-invasive cardiac output and left ventricular ejection volume monitor system in accordance with the principles of the present invention.

Referring to FIG. 7, a portable CO monitoring system measuring CO at the forearm region is disclosed. A cuff would consist of two sections; a thermal section 14 and a pressure section 15. Pressure section 15 would be an inflatable cuff used to gather transient information. Pressure line 16 would have a sensitive pressure transducer 17 that would provide an analog waveform to the A/D (analog to digital) converter 18 which would be digitized and supplied to a digital processor 19 containing the data base discussed above.

Information gained from analyzing this waveform would be systolic and diastolic pressures, heart rate, estimates of plethsymographic volume changes (cuff could have a liquid core) as a function of heart activity, along with the ability to occlude arterial blood flow, as well as the ability to occlude venus blood flow to measure waveforms associated with "filling" of the extremity and to impart an impulse, step or ramp function to the blood flow as discussed above.

Information generated in processor 19 would then be used to adjust the air pressure regulator 20 as desired, via an analog control signal from the D/A (digital to analog) converter 21. The air supply would be from reservoir 22 used to provide a smooth air flow to the cuff avoiding variations associated with the output of compressor 23 varying with load, under control of the compressor controller 24.

The thermal portion 14 of the cuff is supplied with a liquid flow thru an insulated liquid supply line 25, from the peltier diode heat exchanger 26. Two temperature sensors 27 and 28 are located adjacent the thermal portion 14 of the cuff (i.e. RTD, thermocouples, thermistors, etc.) that monitor the inlet temperature $T_w$ and $T_w - \Delta T_w$ as previously described. Temperature sensor outlet lines 29 are supplied to A/D converter 18 where the information is processed to determine $\Delta T_w$, $T_w$ and to generate control signals of a proportional or "PID" control nature to control the peltier diode power supply 30 via analog signals from D/A converter 21. This control loop is used to maintain $T_w$ at its setpoint value.

Liquid flow control is provided by means of a pump 31, and flow is monitored by a flow meter 32 providing signals to A/D converter 18 and, hence, digital processor 19 which maintains control over the flow rate by signals from the D/A converter 21 to control the flow by means of pump controller 33.

Additionally waveform information is received from the blood flow optical sensor 34 which is digitized by A/D converter 18, and provided to digital processor 19. As mentioned above blood flow optical sensor is disposed on a finger, lip, pinna etc. to obtain heart rate information.

The input/output to the system is provided by a keyboard/display unit 35. Specific patient information is entered, on a prompted basis, thru the keyboard, and the results displayed (i.e. LCD liquid crystal, plasma, electroluminesent etc.) In a large system environment, the digital processor 19 would provide continuous information to a display/database system documenting outputs as a function of time. In a clinical monitoring environment, the digital processor 19 would alarm on preset values (i.e. CO, $\overline{CO}$, HR, VLEV, $\overline{VLEV}$, R, etc.).

Figure 8:
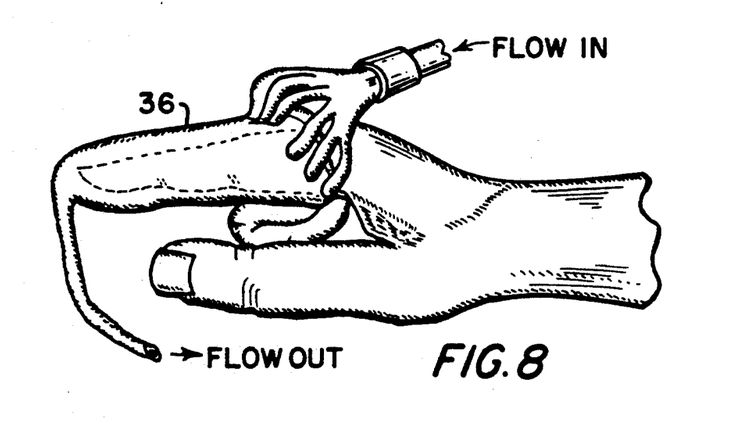

Additionally, several alternative forms of cuffs will be required. In the simplest form a cuff will only have continuous liquid flow, and no ability to alter flows, provide cuff pressure etc. In certain continuous monitoring applications of low criticality patient comfort could be enhanced with small TSU's. FIG. 8 depicts a finger cuff 36 which would be light weight and cause minimal discomfort. It additionally contains the entire extremity, which could be achieved for other extremities i.e. hand, foot, arm/hand. These cuffs would allow the liquid to flow thru molded elastic channels, and the liquid could be in direct contact with the skin surface.

Figures 9, 10:
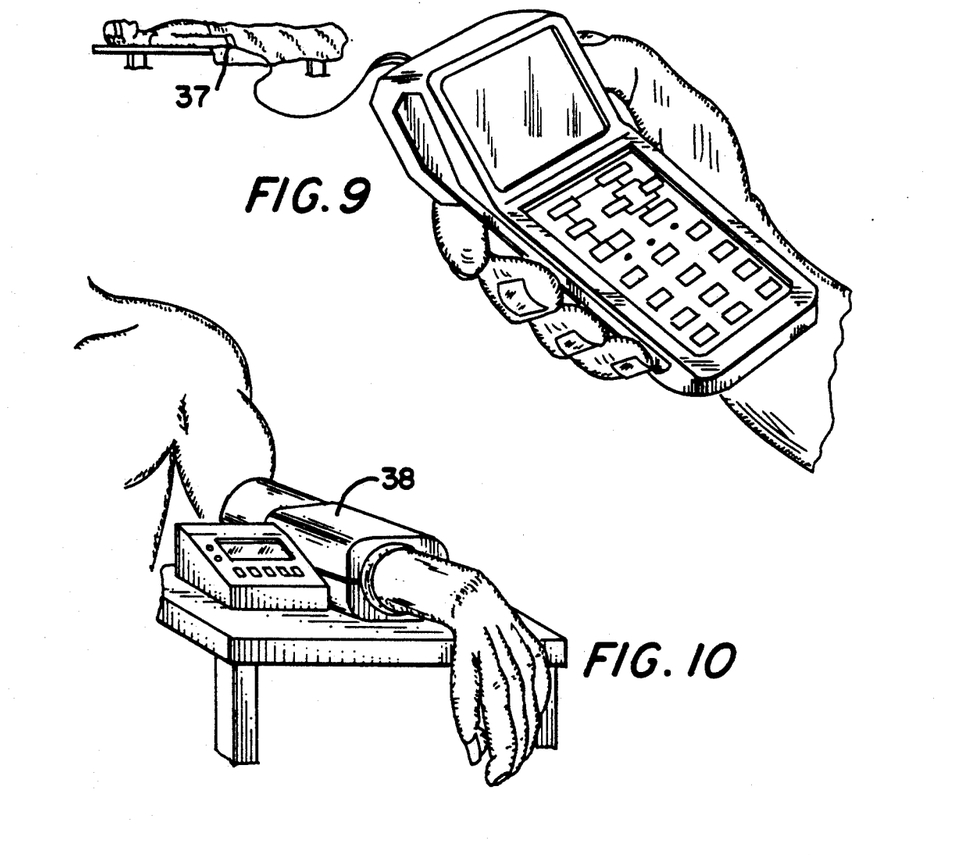

Other cuff applications consider convenience. In an operating room environment, bulky equipment is avoided. Therefore, a cuff 37 that remains on the patient, but is not continually connected to the system could be used. When a reading is required the system would be connected to the cuff 37 as indicated in FIG. 9. In an office environment, convenience and ease of use is required, and a small system with an internal cuff 38 can be configured to meet these requirements as indicated in FIG. 10.

In general the invention will be used to measure total cardiac output, although it will find application for making specific measurements relating to the extremity being monitored.

In situations involving trauma to the head, or hydrocephalus, internal cranial pressures can arise to the point where ischemia becomes significant. This restricted blood flow can be detected with a cuff 39 placed around the neck as shown in FIG. 11. This affords a measurement of flow, which when correlated with body weight etc, can positively indicate restricted perfusion, thru reduced flow.

Figure 12:
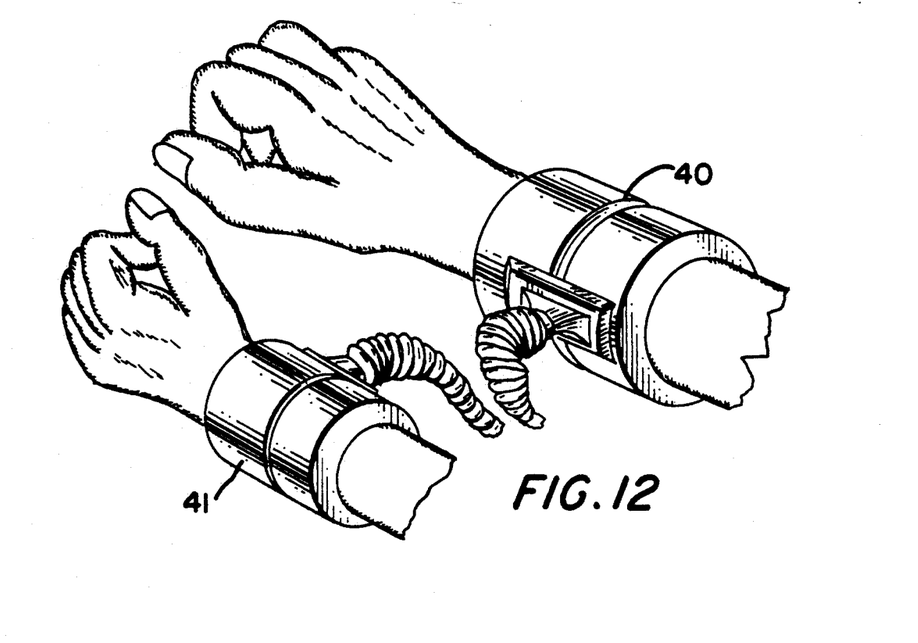

Frequently differential flow becomes an indicator of localized circulatory problems, pathologically or trauma induced. By using two cuffs 40 and 41, one for each extremity, as shown in FIG. 12, high resolution differential measurements become possible.

The data base of the system will be field changeable so that improved algorithms, and more refined data and trend information can be readily installed to upgrade performance.

It is a further objective of this invention to cover extensions of the concept presented, thru the use of alternative techniques to achieve the thermal energy exchange with the blood. For example;

1. Immersing an extremity in rapidly flowing liquid of known thermal characteristics and estimating the energy exchange from the above described techniques as well as measuring the heat exchanged with the liquid and correlating the results.
2. The use of multiple sites on an extremity for both the measurement of heat flow, as well as the introduction of a change in the thermal energy level of the blood. This would allow additional calculations to be made as to the changes in flow along an extremity.
3. Introduction of a thermal change into the blood such as, an injection of a blood expander that has different conductivities than the blood, or introducing energy by radiation in a localized area that would cause a temperature gradient at that point, such as low level microwave radiation.
4. Although the method described discusses flow measurements on an extremity, the invention could find application in an intra operative environment whereby a specific region or organ could be measured. A measurement made at that site could provide a relative measure of local flows there. This measurement when correlated with known flows, measured by other techniques, could provide absolute flows.
5. Mathematical predictive techniques employed to extrapolate results by knowing the general governing relationship. This allows measurements to be accomplished in a shorter time interval. This technique is particularly applicable in the area of thermal dynamics where the long term factors in heat flow equations of a transient nature are frequently of a exponential nature. This allows a few measurements to be made, and the steady state and flows at later times to be predicted.

6. The present invention requires the use of statistical methods to predict not only the absolute cardiac output, but also the tolerances associates with the accuracy of the measurement. Several mathematical techniques of a multivariate nature exist that can be implemented in either hardware or software, to effect the necessary correlations with "known results" and to remove the bias of the measurement technique.

It is the intention of this invention to incorporate these techniques, known to those skilled in the art, in various embodiments, including their application in the absolute cardiac output measurements as well as the accuracy measurements.

While I have described above the principles of my invention in connection with specific apparatus, it is to be clearly understood that this description is made only by way of example and not as a limitation to the scope of my invention as set forth in the objects thereof and in the accompanying claims.

I claim:

1. A non-invasive cardiac output and left ventricular ejection volume monitor system comprising:
   first means adapted to be disposed on a given portion of a patient's body having a fluid passageway therein in juxtaposition with said given portion of said body;
   second means coupled to an inlet of said passageway to cause a fluid to continuously flow therethough at a controllable input temperature and flow rate; and
   third means coupled to said second means and an outlet of said passageway to determine energy transferred between said fluid and said given portion of said body, said determined energy transfer being a measure of said cardiac output.

2. A system according to claim 1, wherein
said first means includes a first cuff encircling said given portion of said body containing said passageway.

3. A system according to claim 2, wherein
said second means includes
   a controllable fluid pump,
   a flow meter coupled to said pump and said third means, and
   a controllable heat exchanger coupled between said flow meter and said inlet to said passageway and to said third means.

4. A system according to claim 3, wherein
said third means includes
   temperature sensors coupled to an outlet of said heat exchanger and said outlet of said passageway to measure the temperature of said fluid at said inlet of said passageway and at said outlet of said passageway, and
   data processor means coupled to said sensors and said flow meter to determine said cardiac output and to generate control signals for said pump and said heat exchanger to provide a desired flow rate for said fluid and a desired temperature for said fluid at said inlet of said passageway.

5. A system according to claim 4, wherein
said processor means generates said control signals to impart a selected one of impulse, step and ramp functions to predetermined ones of said desired temperature and said desired flow rate to enhance measurement of said cardiac output.

6. A system according to claim 5, wherein
said first means further includes
   a second cuff adapted to be encircling said given portion of said body adjacent said first cuff, and
   fourth means coupled to said second cuff and said processor means to pressurize said second cuff and thereby control the flow of blood in said given portion of said body and, hence, the flow of blood through said first cuff.

7. A system according to claim 6, wherein
said processor means controls said fourth means to impart a selected one of impulse, step and ramp functions to pressure applied to said second cuff to enhance measurement of said cardiac output.

8. A system according to claim 1, wherein
said second means includes
   a controllable fluid pump,
   a flow meter coupled to said pump and said third means, and
   a controllable heat exchanger coupled between said flow meter and said inlet to said passageway and to said third means.

9. A system according to claim 8, wherein
said third means includes
   temperature sensors coupled to an outlet of said heat exchanger and said outlet of said passageway to measure the temperature of said fluid at said inlet of said passageway and at said outlet of said passageway, and
   data processor means coupled to said sensors and said flow meter to determine said cardiac output and to generate control signals for said pump and said heat exchanger to provide a desired flow rate for said fluid and a desired temperature for said fluid at said inlet of said passageway.

10. A system according to claim 9, wherein
said processor means generates said control signals to impart a selected one of impulse, step and ramp functions to predetermined ones of said desired temperature and said desired flow rate to enhance measurement of said cardiac output 11. A system according to claim 10, further including
fourth means disposed adjacent said first means on said given portion of said body and coupled to said processor means to control the flow of blood in said given portion of said body and, hence, the flow of blood through said first means.

12. A system according to claim 1, wherein said third means includes
   temperature sensors coupled to said second means and said outlet of said passageway to measure the temperature of said fluid at said inlet of said passageway and at said outlet of said passageway, and
   data processor means coupled to said sensors and said second means to determine said cardiac output and to generate control signals for said second means to provide a desired flow rate for said fluid and a desired temperature for said fluid at said inlet of said passageway.

13. A system according to claim 12, wherein
said processor means generates said control signals to impart a selected one of impulse, step and ramp functions to predetermined ones of said desired temperature and said desired flow rate to enhance measurement of said cardiac output.

14. A system according to claim 13, further including
fourth means disposed adjacent said first means on said given portion of said body and coupled to said processor means to control the flow of blood in said given portion of said body and hence, the flow of blood through said first means.

15. A system according to claim 1, further including fourth means disposed at an extremity of said body and coupled to said third means, said fourth means measuring the heart rate of said body and said third means dividing said cardiac output by said heart rate to provide an indication of said left ventricular ejection volume.

16. A system according to claim 15, wherein said first means includes a first cuff encircling said given portion of said body containing said passageway.

17. A system according to claim 16, wherein said second means includes
   a controllable fluid pump,
   a flow meter coupled to said pump and said third means, and
   a controllable heat exchanger coupled between said flow meter and said inlet to said passageway and to said third means.

18. A system according to claim 17, wherein said third means includes
   temperature sensors coupled to an outlet of said heat exchanger and said outlet of said passageway to measure the temperature of said fluid at said inlet of said passageway and at said outlet of said passageway, and
   data processor means coupled to said sensors and said flow meter to determine said cardiac output and to generate control signals for said pump and said heat exchanger to provide a desired flow rate for said fluid and a desired temperature for said fluid at said inlet of passageway.

19. A system according to claim 18, wherein said processor means generates said control signals to impart a selected one of impulse, step and ramp functions to predetermined ones of said desired temperature and said desired flow rate to enhance measurement of said cardiac output.

20. A system according to claim 19, wherein said first means further includes
   a second cuff encircling said given portion of said body adjacent said first cuff, and
   fifth means coupled to said second cuff and said processor means to pressurize said second cuff and thereby control the flow of blood in said given portion of said body and, hence, the flow of blood through said first cuff.

* * * * *